US008454311B2

(12) United States Patent
Hiremath et al.

(10) Patent No.: US 8,454,311 B2
(45) Date of Patent: Jun. 4, 2013

(54) WIND TURBINE BLADE EDGE MONITORING SYSTEM

(75) Inventors: Vijaykumar Muppayya Hiremath, Bangalore (IN); Vishal Chandra Harupka, Bangalore (IN); D. Mallikarjuna Reddy, Kurnool (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/248,334

(22) Filed: Sep. 29, 2011

(65) Prior Publication Data

US 2012/0141275 A1 Jun. 7, 2012

(51) Int. Cl.
*F03D 11/00* (2006.01)
*F03D 7/00* (2006.01)

(52) U.S. Cl.
USPC .................................... 416/1; 416/61; 356/73

(58) Field of Classification Search
USPC .......... 416/1, 2, 31, 61, 146 R, 232; 324/545, 324/691; 356/329, 73
See application file for complete search history.

(56) References Cited

U.S. PATENT DOCUMENTS 4,026,660 A * 5/1977 Ueda et al. ...................... 416/61
7,896,613 B2 3/2011 Xiong
7,896,615 B2 3/2011 Kappel et al.
2007/0128025 A1 6/2007 Driver
2009/0116962 A1 5/2009 Pedersen et al.
2010/0021297 A1 1/2010 Kuhlmeier
2010/0135796 A1 6/2010 Kavala et al.
2010/0143117 A1* 6/2010 Xiong ............................... 416/1
2011/0135487 A1* 6/2011 Rao et al. ...................... 416/233

FOREIGN PATENT DOCUMENTS

EP 2 258 942 A2 12/2010
WO WO 2010/097485 A1 9/2010

* cited by examiner

*Primary Examiner* — Edward Look
*Assistant Examiner* — Jason Davis
(74) *Attorney, Agent, or Firm* — Dority & Manning, P.A.

(57) ABSTRACT

A monitoring system and associated operational method are operatively configured with a wind turbine for detecting separation of shell members along an edge of a wind turbine rotor blade. The system includes any configuration of sensors disposed within an internal cavity of the rotor blade, with the sensor oriented relative to a leading or trailing edge of the blade and configured to detect a physical characteristic within the blade that is indicative of onset of a separation between the shell members along the monitored edge. A controller is configured to receive signals from the sensor and to initiate an automatic response to a detected separation.

20 Claims, 5 Drawing Sheets

16
20
40
32
25
32
40
40
26
38
24
34
22
34
38

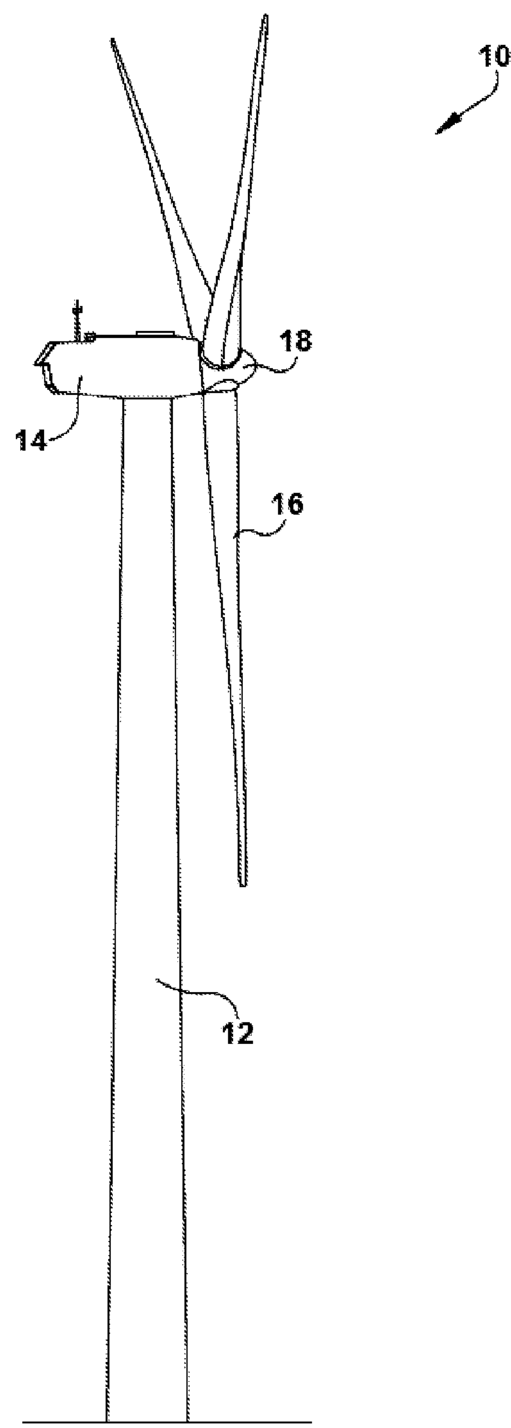
*Fig. -1-*
*Prior Art*

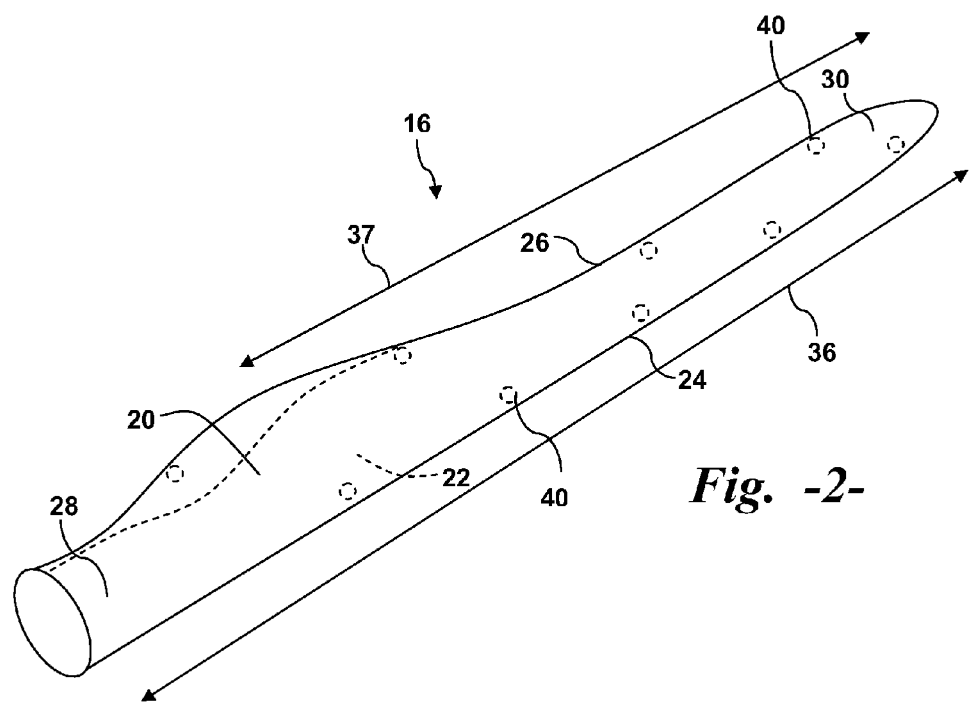
Fig. -2-
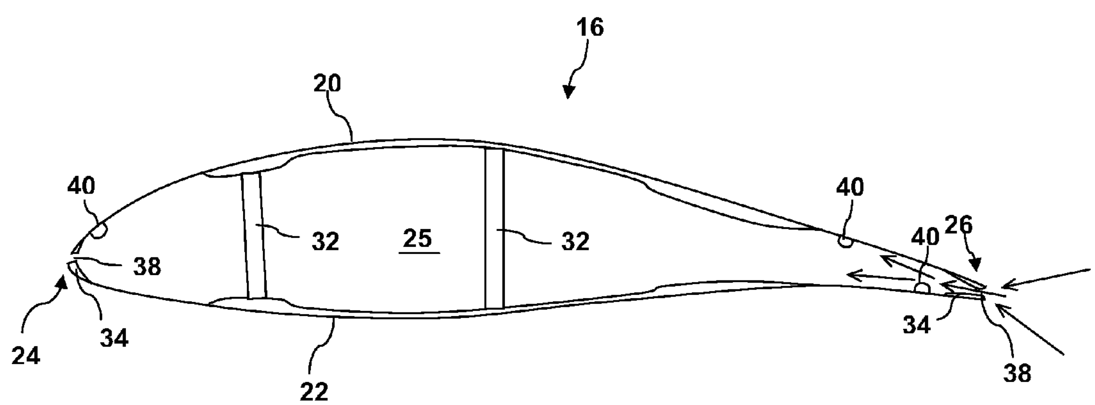
Fig. -3-

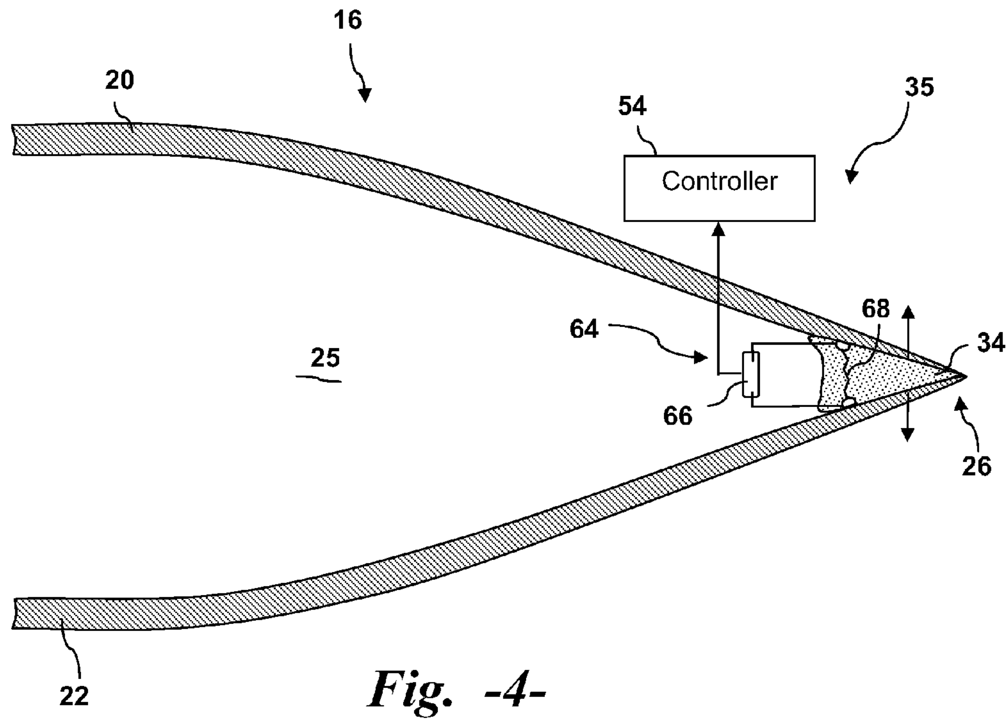
*Fig. -4-*
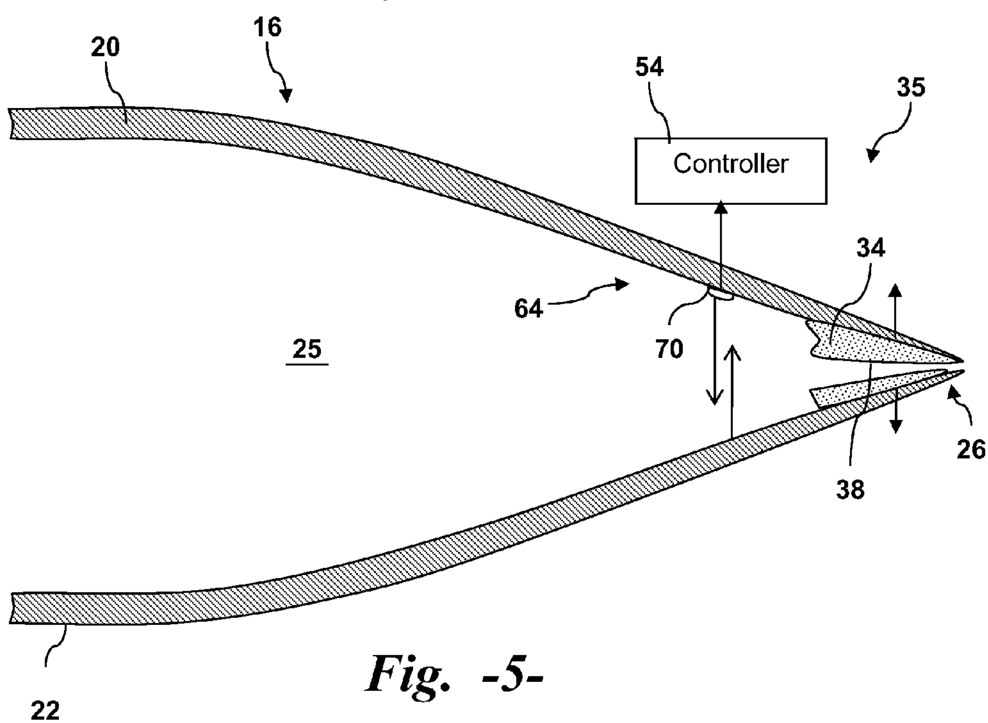
*Fig. -5-*

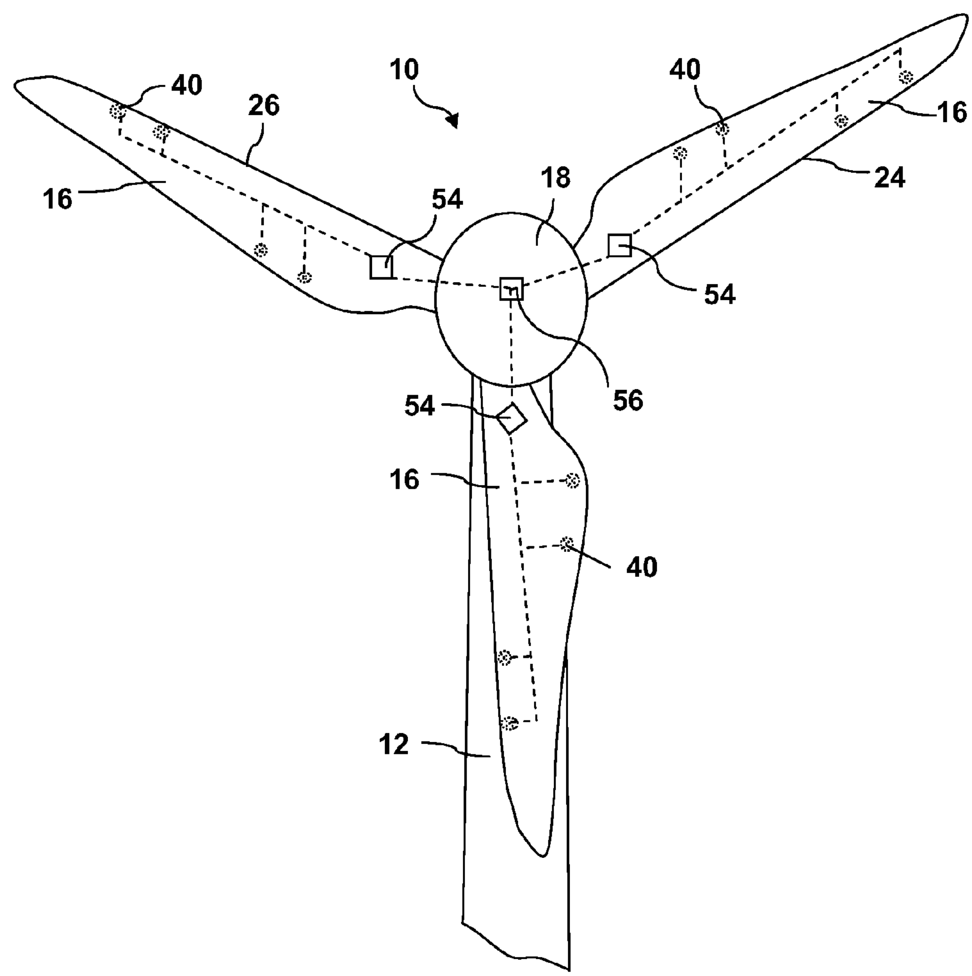
*Fig. -8-*

WIND TURBINE BLADE EDGE MONITORING SYSTEM

FIELD OF THE INVENTION

The present subject matter relates generally to the field of wind turbine rotor blades. More specifically, the subject matter is directed to a monitoring system for early detection of separations that may occur along the leading or trailing edge of a wind turbine rotor blade.

BACKGROUND OF THE INVENTION

The rotor blades are the primary elements of wind turbines for converting wind energy into electrical energy. The blades have the cross-sectional profile of an airfoil such that, during operation, air flows over the blade and produces a pressure difference between the sides. Consequently, a lift force, which is directed from a pressure side towards a suction side, acts on the blade. The lift force generates torque on the main rotor shaft, which is geared to a generator for producing electricity.

The wind turbine rotor blades are generally hollow structures, typically constructed by joining two halves, namely an upper (suction side) shell member and a lower (pressure side) shell member. The shell members are typically bonded together at bond lines along trailing and leading edges of the blade with a suitable bonding material. Any manner of internal support structure, such as one or more spar caps, a shear web, and the like, are also typically bonded to each of the shell members.

A current problem exists in that the shell members may separate along one or both of the edges due to any one or combination of physical variations in the bonding material, including: low bondage strength, manufacturing or application defect, excessive vibrations, cracks in the blade, leading edge erosion, and so forth. Such separation, if not detected early, can lead to complete blade failure, which can be very timely and costly to repair. Monitoring the blade at various locations for the onset of separations and taking necessary preventative measures can avoid this problem.

Accordingly, the industry would benefit from a wind turbine rotor blade edge monitoring system capable of early detection blade separation along one or both edges of the blade.

BRIEF DESCRIPTION OF THE INVENTION

Aspects and advantages of the invention will be set forth in part in the following description, or may be obvious from the description, or may be learned through practice of the invention.

In accordance with various embodiments, a monitoring system is operatively configured with a wind turbine for detecting the occurrence of a separation between the blade shell members along an edge of a rotor blade. The system may be configured with any one or all of the rotor blades and includes a sensor disposed within an internal cavity of the rotor blade. The sensor is configured and oriented relative to the leading or trailing edge of the rotor blade to detect a physical characteristic within the rotor blade that is indicative of onset of a separation between the shell members along the respective edge. A controller is configured to receive signals from the sensor and initiate an automatic response upon determination that a separation has occurred.

The system may include one or, in other embodiments, a plurality of the sensors disposed within the rotor blade so as to monitor the physical characteristic along a longitudinal portion of either or both of the leading or trailing edges.

In a particular embodiment, the sensor is a light sensor configured to detect internal light within the rotor blade resulting from a separation along the respective edge. For example, the controller may be configured to compare the amount of internal light detected by the light sensor to a setpoint value and to initiate the automatic response at a defined differential value. The setpoint value may be a defined value that is programmed in the controller or, in an alternate embodiment, may be supplied by an ambient light sensor that is disposed outside of the rotor blade and in communication with the controller, wherein the controller compares the amount of internal light detected by the internal sensor to the amount of ambient light detected by the ambient sensor and initiates the automatic response at a defined differential value.

In still another embodiment, the sensor may be an acoustic sensor configured within the internal cavity of the rotor blade to detect an increased noise level within the blade resulting from a separation along the respective edge. A separation may be determined by comparing the detected noise level to a threshold or setpoint value, which may be a programmed value. Alternatively, the detected noise level may be compared to an initial baseline noise level, wherein a differential between the noise levels is indicative of a separation.

In a further embodiment, the sensor may be a pressure sensor configured to detect a change in ambient pressure within the rotor blade resulting from a separation along the respective edge. The controller may compare the detected ambient pressure to a setpoint value, and initiate the automatic response at a defined differential value.

In a different embodiment, the sensor may be a distance sensor configured within the internal cavity of the rotor blade to detect a change in the distance between the shell members resulting from a separation along the respective edge. The distance sensor may be an active sensor, such as an IR sensor or ultrasonic sensor.

In another embodiment, the distance sensor may be an electrical sensor that is configured to detect a change in an electrical characteristic generated from a separation along the respective edge. For example, the electrical sensor may include a resistive path that spans between the shell members, the resistive value of which changes when a separation occurs along the respective edge.

The automatic response generated upon detection of a separation may be any one or combination of: generation of a signal indicating a detected separation for any purpose, such as display or control functions; generation of an alarm; or initiation of a wind turbine preventative action, such as stopping or braking the wind turbine rotor.

The invention also encompasses various method embodiments for detecting a separation between shell members along an edge of a wind turbine rotor blade. The method includes monitoring a physical characteristic within an internal cavity of the rotor blade and detecting changes in the physical characteristic that indicate occurrence of a separation along the respective edge, and initiating an automatic response to the detected separation. The monitored physical characteristic may be one or combination of light, sound, or pressure within the rotor blade.

In other embodiments, the method may include monitoring the distance between the shell members adjacent to the respective edge, for example with any suitable passive or active technique.

In response to a detected separation, the method may include any one or combination of: generation of a signal indicating a detected separation, generation of an alarm, or initiation of a turbine preventative action.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWING

A full and enabling disclosure of the present invention, including the best mode thereof, directed to one of ordinary skill in the art, is set forth in the specification, which makes reference to the appended figures, in which:

FIG. 1 is a perspective view of a conventional wind turbine;

FIG. 2 is a perspective view of a rotor blade with a plurality of internal sensors disposed along the leading and trailing edge of the blade;

FIG. 3 is a cross-sectional view of an embodiment of a rotor blade in accordance with aspects of the invention;

FIG. 4 is a partial cross-sectional view of the trailing edge of a rotor blade incorporating an electrical sensor for detecting a separation along the edge;

FIG. 5 is a partial cross-sectional view of the trailing edge of a rotor blade incorporating an active distance sensor for detecting a separation along the edge;

FIG. 8 is a front view of a wind turbine with rotor blades in accordance with aspects of the invention.

DETAILED DESCRIPTION OF THE INVENTION

Figure 6:
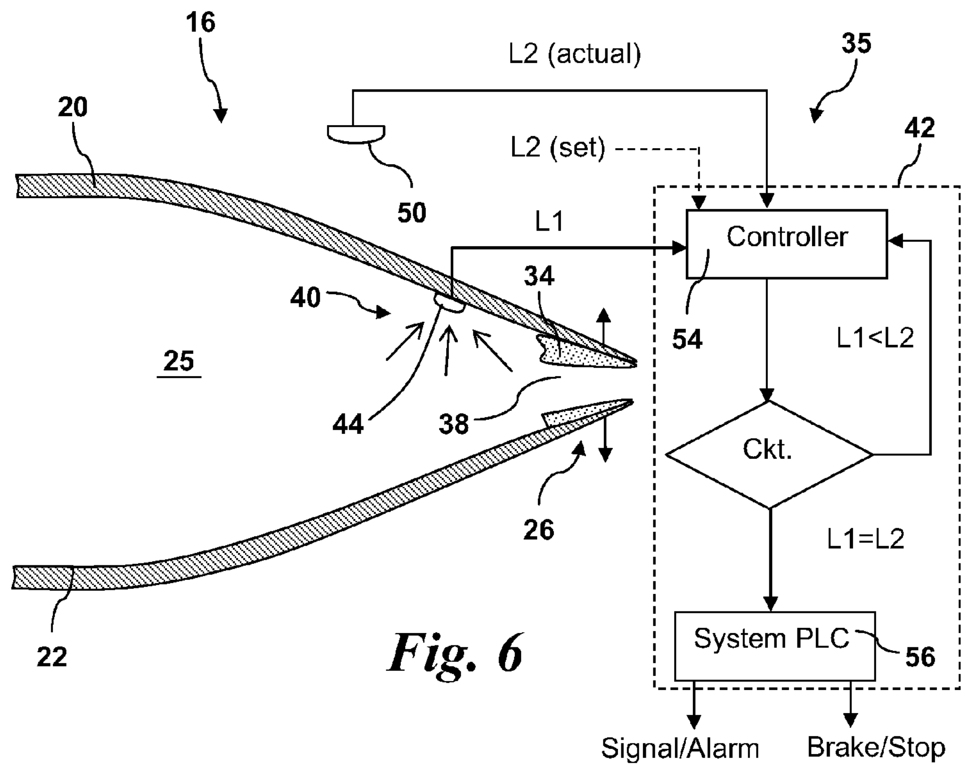
FIG. 6 is a partial cross-sectional view of the trailing edge of a rotor blade incorporating an internal light sensor and associated controller.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 illustrates a wind turbine 10 of conventional construction. The wind turbine 10 includes a tower 12 with a nacelle 14 mounted thereon. A plurality of turbine blades 16 are mounted to a rotor hub 18, which is in turn connected to a main flange that turns a main rotor shaft. The wind turbine power generation and control components are housed within the nacelle 14. The view of FIG. 1 is provided for illustrative purposes only to place the present invention in an exemplary field of use. It should be appreciated that the invention is not limited to any particular type of wind turbine configuration.

FIG. 2 is a more detailed view of a wind turbine blade 16. The blade 16 includes an upper shell member 20 and a lower shell member 22. The upper shell member 20 may be configured as the suction side surface of the blade 16, while the lower shell member 20 may be configured as the pressure side surface of the blade. The blade 16 includes a leading edge 24 and a trailing edge 26, as well as a root portion 28, and a tip portion 30. As is well known in the art, the upper shell member 20 and lower shell member 22 are joined together at a bond line 36 along the leading edge 24 and a bond line 37 at the trailing edge 26. In formation of these bond lines 36, 37, a bond paste 34 (FIG. 3) is applied in viscous form between the mating laminate surfaces of the upper shell member 20 and lower shell member 22 along the length of the bond lines 36, 37. It should be appreciated that the term "bond paste" is used herein in a generic sense to encompass any type of adhesive or bonding material that is applied in an initially flowable state. The particular type of bond paste 34 is not particularly relevant to the present invention, and any suitable type of epoxy, compound, or other material may be used in this regard.

The bond paste 34 is typically applied in a sufficient quantity and pattern to ensure that the bond lines 36, 37 have a sufficient bonded surface area between the components along the length of the respective bond lines 36, 37. However, due to any number of factors, the bond paste 34 may fail (e.g., separate from the shell members, crack, break, etc.) and separations 38 (FIG. 3) can form between the shell members 20, 22 along the edges 24, 26. As discussed above, if left uncorrected, these separations can quickly lead to a complete failure of the blade 16.

The wind turbine blades 16 depicted in FIGS. 2 and 3 incorporate aspects of embodiments of the present invention. The blade 16 includes any manner of internal support structure 32, such as one or more shear webs 32, spar cap, and the like. The upper 20 and lower 22 shell members are joined at the leading and trailing edges 24,26 by a bond paste 34. Referring to FIG. 3, a failure of the bond paste 34 is depicted at the leading and trailing edges 24, 26 such that a separation 38 is created between the shell members 20, 22 at each of the edges 24, 26. One or more sensors 40 are disposed within the internal cavity 25 of the blade at a position and orientation relative to either or both of the leading edge 24 and trailing edge 26 so as to detect a physical characteristic within the rotor blade 16 that is indicative of the onset of a separation 38 between the shell members. This physical characteristic may be any one or combination of measurable or detectable events or parameters that change as a result of the onset of the separation 38 within the effective range of the sensor 40. It is within the scope and spirit of the invention to utilize any number, pattern, and configuration of the sensors 40 along either or both of the edges 24, 26. For example, multiple sensors 40 may be positioned generally adjacent to the trailing edge 26, as depicted in FIG. 3, while one or more of the sensors 40 may also be positioned relatively adjacent to the leading edge 24.

In the embodiment of FIG. 3, the sensors 40 may be any manner of suitable light detectors that react to an increase in the amount of light within the internal cavity 25 of the blade 16 as a result of light being emitted into the cavity 25 through the separation 38, as depicted by the lines in FIG. 3.

FIG. 6 depicts a more detailed view of a monitoring system 35 in accordance with a particular embodiment of a light sensor configuration at the trailing edge 26 of a blade 16. In this embodiment, the sensor 40 is a light sensor 44 that is disposed on an inner surface of either or both of the shell members 20, 22 at a location so as to detect an increase in light within the cavity 25 resulting from the separation 38. The light sensor 44 may be, for example, any one or combination of known light detectors, including a photoresistor, photoconductor, photodetector, or photovoltaic device.

A controller 54 is in operable communication with the sensor 44 and receives a signal from the sensor 44 indicative of the amount of light within the cavity 25. The controller 54 may be associated with all of the sensors 40 within a blade 16, as depicted in FIG. 8. In alternate embodiments, a controller 54 may be associated with each of the sensors 44. The controller 54 may be a component of an overall control system 42 associated with the wind turbine to process the signals from the light sensors 44 for any purpose, including corrective action, alarms, data generation and recording, and so forth. For example, still referring to FIG. 6, the controller 54 may be in operable communication with a wind turbine system controller 56 that controls various operational features of the wind turbine 10. The system controller 56 may use information from the controller 54 (or directly from the sensors 40) to initiate an automatic response when onset of a separation 38 is detected. This automatic response may be any one or combination of corrective actions, signals, alarms, and so forth. The system controller 56 may, for example, generate a brake or stop signal that causes the rotor hub 18 (FIG. 1) to rotationally lock and prevent further rotation of the blades 16 in order to prevent any further damage to the blades or tower. The controller 56 may simultaneously generate any manner of alarm or other signal to a local or remote monitoring station. It should be appreciated that the present invention is not limited to any particular use or type of automatic response to a detected separation 38.

Referring again to FIG. 6, the monitoring system 35 illustrated therein may include an ambient light sensor 50 that is disposed at some external location relative to the blade 16, for example on the nacelle, rotor hub, or any other component of the wind turbine 10. The ambient light sensor 50 detects ambient light conditions at the blade 16, and generates an actual light signal L2 (actual) that is supplied to the controller 54. As depicted in FIG. 6, a comparison may be conducted by any suitable component of the control system 42 between the ambient light L2 (actual) and the internal light L1 detected by sensor 44. When the internal light L1 is about equal to the ambient light L2 (actual), then this may be an indication that a separation 38 has occurred at the trailing edge 26. An appropriate signal may be generated and sent to the system controller 56 for any one or combination of automatic responses, as discussed above.

In an alternative embodiment also depicted in FIG. 6, a programmed input value L2 (set) may be programmed into the controller 54, wherein a comparison is made between the actual internal light L1 and the programmed value L2 (set). In this embodiment, a separate ambient light detector is not needed, and the programmed value L2 (set) may be varied or adjusted accordingly for any number of reasons, such as location of the wind turbine, climate conditions, time of year, and so forth.

Figure 7:
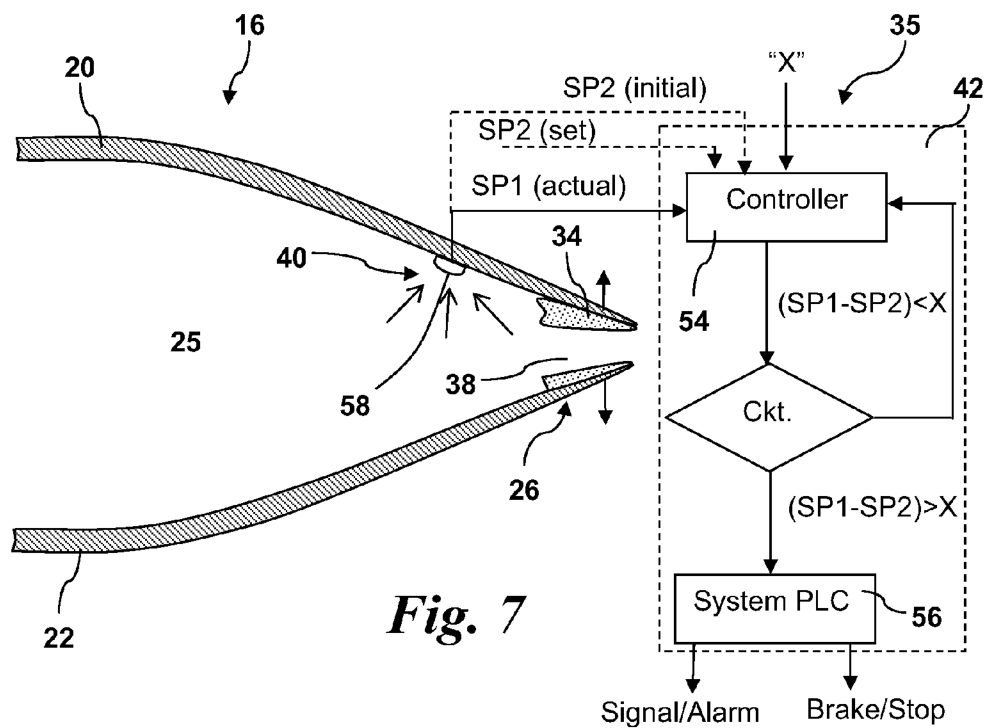
FIG. 7 is a partial cross-sectional view of the trailing edge of a rotor blade incorporating an acoustic or pressure sensor and associated controller.

FIG. 7 depicts an embodiment of a monitoring system 35 wherein the sensor 40 is any manner of suitable acoustic sensor 58 that is configured to detect an increased noise level within the internal cavity 25 of the blade 16 resulting from a separation 38 at the trailing edge 26. The acoustic sensor 58 may be any manner of microphone, such as a carbon (resistive), capacitive (piezoelectric), or moving-coil microphone. Moving-coil microphone devices use a magnet and a coil attached to a diaphragm, as is known in the art. It should be appreciated that the invention is not limited to any particular type of sound sensor or detection device. An actual sound signal SP1 (actual) is generated by the sensor 58 and transmitted to the controller 54. This signal is compared to either a setpoint or threshold value SP2 (set) that may be programmed into the controller 54, or to an initial value SP2 (initial) generated by the sensor 58, for example during installation of the wind turbine, construction of the blade, or any other suitable time wherein a base line sound signature may be obtained. The control system 42 conducts a comparison between actual sound SP 1 (actual) detected by sensor 58 and the initial or set sound value SP2 (set). When the difference between these sound values exceeds a defined value (X), then a signal is sent to the system controller 56 indicating that a separation 38 may have occurred at the trailing edge 26, wherein any one or combination of automatic responses may be generated, as discussed above.

In an alternate embodiment, the actual noise level within the blade cavity 25 detected by sensor 58 may simply be compared in the controller 54 to a set point value (also represented by "X"). In other words, in this embodiment, it is not necessary to determine a differential between the actual sound signal SP1 (actual) and an initial baseline sound signal.

In still a further embodiment, the monitoring system 35 may utilize any manner of pressure sensor within the internal cavity 25 of a blade 16. For example, referring to FIG. 7, sensor 58 may also represent a pressure sensor that detects an actual pressure condition within the internal cavity 25, with the actual pressure changing as a result of a separation 38 at the trailing edge 26. The analysis discussed above with respect to FIG. 7 and the embodiment wherein the sensor 58 is an acoustic sensor applies to the embodiment wherein the sensor 58 is a pressure sensor, and need not be repeated herein.

Referring to FIGS. 4 and 5, embodiments of a monitoring system 35 may utilize a sensor 40 that detects a change in the distance between the shell members 20, 22 resulting from a separation along the respective edge, such as the trailing edge 26. For example, in the embodiment of FIG. 4, the distance sensor 64 is an electrical sensor 66 configured to detect a change in an electrical characteristic generated from a separation along the trailing edge 26 (as indicated by the arrows in FIG. 4). In this particular embodiment, the electrical sensor 66 includes a resistive path 68, such as a resistive wire, that spans between the shell members 20, 22. This wire 68 may be, for example, embedded in the bond paste 34, or separate from the bond paste 34 at any location such that a separation of the shell members 20, 22 results in a stretching or breaking of the resistive path 68 and corresponding change in the resistive value of the resistive path 68. For example, a complete separation along the trailing edge 26 may result in a brake of the resistive path 68, which will be detected as an open circuit by the electrical sensor 66. Less than a complete brake or open circuit along the path 68 may also be detected by the sensor 66 so long as the resistant value of the path 68 changes as a function of the degree of separation between the shell members 20, 22.

In the embodiment of FIG. 5, the distance sensor 64 is depicted as an active sensor 70. The active sensor 70 may, for example, be any manner of suitable transceiver device that transmits a signal to the opposite shell member 22 and receives a return signal. The timing of the return signal will indicate whether or not a separation 38 has occurred along the trailing edge 26. Any manner of suitable ultrasonic sensor, laser sensor, or other type of active transceiver devices may be utilized in this regard.

FIG. 8 is a partial view of a wind turbine 10 with blades 16 that incorporate multiple sensors 40 along the respective leading 24 and trailing edges 26 of the blades 16 in accordance with aspects discussed above. A respective controller 54 is depicted with each blade 16. All of the sensors 40 configured with a particular blade 16 may be in communication with the single controller 54, with the plurality of controllers 54 in communication with the system controller 56. The system controller 56 may be located, for example, in the nacelle 14 (FIG. 1), tower 12, a remote location, or any other suitable location. The types of sensors 40 utilized with the blade 16 may be any one or combination of the devices discussed above.

The present invention also encompasses various method embodiments in accordance with the aspects discussed above. For example, a method is provided for detecting a separation between shell members along an edge of a wind turbine rotor blade. The method may include monitoring a physical characteristic within an internal cavity of the rotor blade and detecting changes in the physical characteristic that indicate occurrence of a separation along a respective edge. In response to a detected separation, any manner of automatic response may be generated, including an alarm, signal, corrective action, and the like, as discussed above.

The monitored physical characteristic in the method embodiments may include any one or combination of light, sound, or pressure within the rotor blade.

In an alternate method embodiment, the monitored physical characteristic may be the distance between the shell members adjacent to the respective edge. This distance may be monitored with an active sensing method, or a passive sensing method. For example, the distance may be monitored by detecting a change in an electrical parameter induced by a separation along the respective edge.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A monitoring system operatively configured with a wind turbine for detecting separation of shell members along an edge of a wind turbine rotor blade, said system comprising:

a sensor disposed within an internal cavity of a rotor blade, said sensor oriented relative to a leading or trailing edge of said rotor blade and configured to detect a physical characteristic within said rotor blade that is indicative of onset of a separation between said shell members along said respective edge; and a controller configured to receive signals from said sensor and initiate an automatic response to a detected separation.

2. The monitoring system as in claim 1, further comprising a plurality of said sensors disposed within said rotor blade, said sensors disposed so as to monitor said physical characteristic along at least a portion of either or both of said leading or trailing edges.

3. The monitoring system as in claim 1, wherein said sensor is a light sensor configured to detect internal light within said rotor blade from a separation along said respective edge.

4. The monitoring system as in claim 3, wherein said controller is configured to compare the amount of internal light detected by said light sensor to a setpoint value and to initiate the automatic response at a defined differential value.

5. The monitoring system as in claim 1, further comprising an ambient light sensor disposed outside of said rotor blade and in communication with said controller, wherein said controller is configured to compare the amount of internal light detected by said internal sensor to the amount of ambient light detected by said ambient sensor and to initiate the automatic response at a defined differential value.

6. The monitoring system as in claim 1, wherein said sensor is an acoustic sensor configured to detect an increased noise level within said rotor blade from a separation along said respective edge.

7. The monitoring system as in claim 6, wherein said controller is configured to compare the noise level detected by said acoustic sensor to a threshold or initial baseline noise level.

8. The monitoring system as in claim 1, wherein said sensor is a pressure sensor configured to detect a change in ambient pressure within said rotor blade from a separation along said respective edge, compare the detected ambient pressure to a threshold value, and initiate the automatic response at a defined differential value.

9. The monitoring system as in claim 1, wherein the automatic response is any one or combination of: generation of a signal indicating a detected separation, generation of an alarm, or initiation of a turbine preventative action.

10. The monitoring system as in claim 9, wherein said controller is configured to initiate braking of said wind turbine rotor in response to a detected separation.

11. A monitoring system operatively configured with a wind turbine for detecting separation of shell members along an edge of a wind turbine rotor blade, said system comprising:

a sensor disposed within an internal cavity of a rotor blade, said sensor oriented relative to a leading or trailing edge of said rotor blade and configured to detect a physical characteristic within said rotor blade that is indicative of onset of a separation between said shell members along said respective edge;

a controller configured to receive signals from said sensor and initiate an automatic response to a detected separation; and wherein said sensor is a distance sensor configured to detect a change in distance between said shell members from a separation along said respective edge.

12. The monitoring system as in claim 11, wherein said distance sensor is an active sensor.

13. The monitoring system as in claim 11, wherein said distance sensor is an electrical sensor configured to detect a change in an electrical characteristic generated from a separation along said respective edge.

14. The monitoring system as in claim 13, wherein said electrical sensor comprises a resistive path that spans between said shell members and changes its resistive value when a separation occurs along said respective edge.

15. A method for detecting a separation between shell members along a leading or trailing edge of a wind turbine rotor blade, the method comprising monitoring a physical characteristic within an internal cavity of the rotor blade and detecting changes in the physical characteristic that indicate occurrence of a separation along the respective leading or trailing edge; and initiating an automatic response to the detected separation.

16. The method as in claim 15, wherein the monitored physical characteristic is any one or combination of light, sound, or pressure within the rotor blade.

17. The method as in claim 15, wherein the monitored physical characteristic is distance between the shell members adjacent to the respective edge.

18. The method as in claim 17, wherein the distance is monitored with an active sensing method.

19. The method as in claim 17, wherein the distance is monitored by detecting changes in an electrical parameter induced by a separation along the respective edge.

20. The method as in claim 15, wherein the automatic response is any one or combination of: generation of a signal indicating a detected separation, generation of an alarm, or initiation of a turbine preventative action.

* * * * *